United States Patent
Code (10) Patent No.: US 8,734,559 B2
(45) Date of Patent: May 27, 2014

(54) MODERATION OF ANIMAL ENVIRONMENTS

(75) Inventor: Kenneth R. Code, Edonton (CA)

(73) Assignee: Biolargo Life Technologies, Inc., Irvine, CA (US)

( * ) Notice: Subject to any disclaimer, the term of this patent is extended or adjusted under 35 U.S.C. 154(b) by 449 days.

(21) Appl. No.: 13/116,816

(22) Filed: May 26, 2011

(65) Prior Publication Data

US 2011/0296883 A1 Dec. 8, 2011

Related U.S. Application Data

(63) Continuation-in-part of application No. 12/220,484, filed on Jul. 24, 2008, and a continuation-in-part of application No. 11/973,933, filed on Oct. 11, 2007, now Pat. No. 8,021,610, which is a continuation-in-part of application No. 11/516,960, filed on Sep. 7, 2006, now Pat. No. 7,867,510, and a continuation-in-part of application No. 11/516,958, filed on Sep. 7, 2006, now abandoned.

(60) Provisional application No. 61/396,836, filed on Jun. 2, 2010, provisional application No. 60/961,903, filed on Jul. 25, 2007, provisional application No. 60/850,976, filed on Oct. 11, 2006.

(51) Int. Cl.
| | |
|---|---|
| *C02F 1/76* | (2006.01) |
| *C05F 3/00* | (2006.01) |
| *C05F 11/00* | (2006.01) |
| *C05C 11/00* | (2006.01) |
| *C05D 7/00* | (2006.01) |

(52) U.S. Cl.
USPC ............... 71/11; 71/15; 71/21; 71/31; 71/54; 71/61; 71/DIG. 903; 119/171; 210/753

(58) Field of Classification Search
USPC ............ 71/11, 15, 21, 31, 54, 61, DIG. 903; 119/171–174; 210/753
See application file for complete search history.

(56) References Cited

U.S. PATENT DOCUMENTS

| | | | |
|---|---|---|---|
| 5,669,894 | A | 9/1997 | Goldman et al. |
| 5,837,789 | A | 11/1998 | Stockhousen et al. |

(Continued)

FOREIGN PATENT DOCUMENTS

WO WO02058748 8/2002

OTHER PUBLICATIONS

Gottardi, W. "Iodine and Iodine Compounds," in Block, SS., Disinfection, Sterilization, and Preservation, 4th edition. (Lea & Febiger, 1991), Chapter 8, pp. 152-165, and 166.

(Continued)

*Primary Examiner* — Wayne Langel
(74) *Attorney, Agent, or Firm* — Mark A. Litman & Associates, P.A.

(57) ABSTRACT

An environment is moderated in an area where animal wastes are collected in a fluid containing compartment. Animal wastes are collected in a fluid containing compartment. The animal wastes are of the type that generate or provide in or above the fluid containing compartment at least one waste selected from the group consisting of carbon dioxide, hydrogen sulfide, ammonia, mercaptans and organic acids. A combination is provided of i) a polymer capable of absorbing at least ten times its weight in water (preferably a superpolymer) and ii) a combination of salts that react to liberate $I_2$. At least one waste is flocculated with liberated $I_2$ (and any cations from the reactive salts) to form a flocculent that has reduced odor and reduced microbial content. The flocculent may be used as a fertilizer.

17 Claims, 5 Drawing Sheets

Natural settling of liquid swine manure.

(56) References Cited

U.S. PATENT DOCUMENTS

| | | | |
|---|---|---|---|
| 6,967,261 B1 | 11/2005 | Soerens et al. | |
| 7,462,753 B2 | 12/2008 | Ma et al. | |
| 7,528,291 B2 | 5/2009 | Herfert et al. | |
| 7,541,395 B2 | 6/2009 | Reimann et al. | |
| 7,726,260 B1* | 6/2010 | Yananton | 119/171 |
| 2004/0077744 A1 | 4/2004 | Naylor et al. | |
| 2006/0219183 A1* | 10/2006 | Yasukawa | 119/171 |
| 2008/0022940 A1* | 1/2008 | Kirsch et al. | 119/173 |
| 2008/0063560 A1 | 3/2008 | Code | |
| 2008/0063694 A1 | 3/2008 | Code | |
| 2008/0095812 A1 | 4/2008 | Code | |
| 2008/0121592 A1 | 5/2008 | Code | |
| 2008/0145391 A1 | 6/2008 | Nelson et al. | |
| 2008/0193562 A1 | 8/2008 | Code | |
| 2009/0028915 A1 | 1/2009 | Code | |
| 2009/0084322 A1* | 4/2009 | Axelrod | 119/171 |

OTHER PUBLICATIONS

Waste Management Factsheet, "Hog Slurry Separation with a Centrifuge," Ministry of Agriculture, Food and Fisheries, Order No. 382.340-1, Mar. 1994. pp. 1-2.

Finney, L., et al., "X-ray Fluorescence Microscopy Reveals Large-scale Relocalization and Extracellular Translocatoin of Cellular Copper During Angiogenesis," in Proceedings from the National Academy of Sciences (PNAS), (The National Academy of Sciences of the USA 2007) Feb. 13, 2007, vol. 104, No. 7 pp. 2247-2252. [Available online www.pnas.org/cgi/doi/10.1073/pnas.0607238104].

Chelme-Ayala, P., "Advanced Treatment of Liquid Swine Manure Using Physico-chemical treatment," in Journal of Hazardous Materials 186, (Elsevier B.V. 2011) pp. 1632-1638.

* cited by examiner

Figure 1. Natural settling of liquid swine manure.

Figure 2. Effect of mixing speed on TSS removal. Experimental condition: dilution = 1:5, $TSS_0$ = 470 mg/L, $pH_0$ = 7.78, $SAP_0$ = 0.5 mg/L.

Figure 3. Effect of mixing time on TSS removal. Experimental condition: dilution = 1:5, $TSS_0$ = 200 mg/L, $pH_0$ = 11.07, Speed = 200 rpm, $SAP_0$ = 0.5 g/L.

Figure 4. TSS removal using supernatant without dilution. Experimental conditions: $TSS_0$ = 2300 mg/L, $pH_0$ = 7.36, speed: 200 rpm, mixing time = 5 min.

Figure 5. TSS removal using supernatant diluted five times. Experimental conditions: $TSS_0$ = 313 mg/L, $pH_0$ = 11.01, speed: 200 rpm, mixing time = 5 min.

Figure 6. Removal of ammonia using CupriDyne™ tables. Experimental conditions: dilution = 1:1, $ammonia_0$ = 1436 mg/L N, $pH_0$ = 7.69, $SAP_0$ = 1.25 g/L

Figure 7. TOC Removal using CupriDyne™ tables. Experimental conditions: dilution = 1:1, $TOC_0$ = 1732 mg/L C, $pH_0$ = 7.69, $SAP_0$ =1.25 g/L.

Figure 8. Reduction of ammonia using CupriDyne™ tables. Experimental conditions: dilution=1:5, $pH_0$ = 11.01, $ammonia_0$ = 325 mg/L N, $SAP_0$ =0.5 g/L.

Figure 9. TOC Removal using CupriDyne™ tables. Experimental conditions: dilution=1:5, $TOC_0 = 509$ mg//L C, $pH_0 = 11.01$, $SAP_0 = 1.25$ g/L.

Figure 10. Toxic effects of treated supernatant on *Vibrio fischeri*. Experimental conditions: dilution=1:1, $pH_0 = 7.58$, test: 8% screening test, Phase 2.

MODERATION OF ANIMAL ENVIRONMENTS

RELATED APPLICATIONS DATA

This application claims priority from U.S. Provisional Patent Application Ser. No. 61/396,836, filed Jun. 2, 2010, which in turn claims priority as a Continuation-in Part application from U.S. patent application Ser. No. 12/220,484, filed Jul. 28, 2008, which in turn claims priority from U.S. Provisional Application Ser. No. 60/961,903, filed Jul. 25, 2007, which in turn claims priority as a Continuation-in-Part application of U.S. Provisional Patent Application Ser. No. 60/850,976, filed Oct. 11, 2006 (now U.S. patent application Ser. No. 11/973,933) which is in turn a Continuation-in-Part of both of U.S. patent application Ser. No. 11/516,960, filed Sep. 7, 2006 and U.S. patent application Ser. No. 11/516,958, filed Sep. 7, 2006.

BACKGROUND OF THE INVENTION

1. Field of the Invention

The present invention relates to the field of moderation of environments where animal are stored or housed and release waste into an area adjacent, under or into the environment. The invention relates to moderating effects of microbes and gaseous emissions from the waste and to the ability to use bound waste safely and effectively in agricultural applications.

2. Background of the Art

Modern livestock techniques involve the sheltering of large numbers of animals in confined areas. Whether with poultry (chicken, turkeys, ducks and geese) or mammals (cattle, pigs, sheep, goats, horses and the like), high density or concentrated housing of animals is a cost efficient method of producing livestock, but that density often creates adverse conditions for the growth and health of the animals and for workers. The density of waste, the concentration of microbes and the volume of emissions from the stored wastes greatly increase along with the animal density in storage, and the difficulty in moderating or correcting that environment increases with the larger scale of the livestock system.

Even mythology has attempted to address the problems of maintaining a clean environment for large stables in the Fifth Labor of Hercules. For the fifth labor, Eurystheus ordered Hercules to clean up King Augeas' stables. Eurystheus made Hercules' task even harder, requiring him to clean up after all of the cattle of Augeas in a single day. King Augeas owned more cattle than anyone in Greece and he had many herds of cows, bulls, goats, sheep and horses. First Hercules tore a first opening in one wall of the cattle-yard where the stables were. Then he made another opening in the wall on the opposite side of the yard. Next, he dug wide trenches to two rivers which flowed nearby and then turned the course of the rivers into the yard. The rivers rushed through the stables, flushing them out, and all the mess flowed out the hole in the wall on other side of the yard.

Modern livestock management has mimicked this technique, with large animal waste storage areas provided under the flooring animal stalls and pens, and the storage areas may be cleaned only a few times a year by flushing out the storage areas with water and then scrubbed. The waste is highly aromatic and microbe laden and is costly to dispose of.

The nature of the problems caused by large concentration housing of animals is quite significant. It has been observed that, for example, with hog raising environments, the high emissions of ammonia from the wastes damages the lungs of growing piglets and slows their rate of growth. Carbon dioxide emissions from bovine animals are even indicated as significant in the green house effect. Emissions from poultry have been found to be a mechanism for avian microbe transmission between poultry and potentially to humans in cross-over viruses.

The following Published U.S. Patent Application Documents disclose related technology for treatment of various situations and conditions that have been developed by the present inventor and are incorporated herein by reference, Published U.S. Patent Documents 20090028915; 20080193562; 20080145391; 2008121592; 20080095812; 20080063694; and 20080063560. Some of these references disclose the combination of cupric sulfate and potassium iodide combined with superabsorbent polymers, and includes disclosure of adding those materials directly onto flooring and bedding in stalls for animals. This bedding, usually in single animal stalls, must be turned and removed as is bedding, but delays the time period between bedding replacement.

U.S. Pat. No. 7,528,291 (Herfert et al.) describes a color-stable superabsorbent polymer having long-term color stability, and methods of manufacturing the polymer, are disclosed. The color-stable superabsorbent polymer is prepared in the essential absence of a persulfate, and is subjected to a low dose of ultraviolet radiation. The resulting superabsorbent polymer resists color degradation during periods of extended storage, even at an elevated temperature and humidity.

U.S. Pat. No. 5,837,789 (Stockhousen) describes superabsorbing polymers for watery liquids, processes used in their production and their application. The polymers, based on monomers containing carboxylate groups and obtained by a special combination of cross-linking agents and other comonomers, show a combination of properties never attained before with regard to absorption rate, high retention at high absorption under pressure, low soluble content and good permeability of the gel layer for watery liquids under pressure load and stable surface cross-linkage.

U.S. Pat. No. 5,669,894 (Goldman et al.) describes absorbent polymers and materials useful in the containment of fluids, that have at least one region containing hydrogel-forming absorbent polymer in a concentration of from about 60 to 100% by weight and providing a gel-continuous fluid transportation zone when in a swollen state. This hydrogel-forming absorbent polymer has: (a) a Saline Flow Conductivity (SFC) value of at least about $30 \times 10^{-7}$ cm.sup.3 sec/g; (b) a Performance under Pressure (PUP) capacity value of at least about 23 g/g under a confining pressure of 0.7 psi (5 kPa); and (c) a basis weight of at least about 10 gsm. In addition, the region where this hydrogel-forming absorbent polymer is present has, even when subjected to normal use conditions, sufficient wet integrity such that the gel-continuous zone substantially maintains its ability to acquire and transport fluids through the gel-continuous zone.

Published U.S. Patent Publication 20040077744 (Naylor) describes a process of preparing water soluble or water swellable polymer comprising the steps: a) forming an aqueous mixture comprising, i) a water soluble ethylenically unsaturated monomer or blend of monomers and, ii) at least one first ultra-violet initiator, iii) at least one second ultra-violet initiator; b) effecting polymerisation by subjecting the aqueous mixture formed in step (a) to irradiation by ultraviolet light at an intensity of up to 1,000 micrometers $Wcm^{-2}$; subjecting the product of step (b) to irradiation by ultraviolet light of greater than 1,000 micrometers $Wcm^{-2}$, characterised in that a significant amount of the first initiator(s) is/are activated in step (b) and a significant amount of the second initiator(s) is/are activated in step (c). The process is particularly suitable for making highly effective water soluble and water swellable polymers useful as flocculants, coagulants, rheology modifiers, dispersants, superabsorbents and binders etc.

U.S. Pat. No. 7,462,753 (Ma) discloses a nano-silver wound dressing consisting of a skin contact layer made from hydrophilic cloth and directly contacting a wound on the surface of the skin, a disinfecting (or bactericidal) antitoxic layer made from activated charcoal cloth impregnated with nanocrystalline silver, a blood absorbing and styptic layer made from a superabsorbent polymer non-woven cloth, an isolation layer made from a composite fabric with a pore size of less than 5 micrometers and an elastic bandage for fixing a main body on the site of wound. Edges of the isolation layer and the skin contact layer are integrated to form a main body while the disinfecting (or bactericidal) antitoxic layer as well as the blood absorbing and styptic layer are separated from each other and both enclosed inside the main body.

U.S. Pat. No. 6,967,261 (Soereus) describes a bandage or wrap with antibiotics therein. It is further described that an included nonwoven material may be treated to be hydrophilic or may include superabsorbent materials.

U.S. Pat. No. 7,541,395 (Reimann) describes a process for producing an absorbent polymer including a first mixing event, in which a plurality of absorbent polymer particles (1) are mixed with a liquid (2) and a second mixing event, in which the liquid (2) is homogenized within the interior of the polymer particles. The polymer particles (1) in the first mixing event are mixed with a speed such that the kinetic energy of the individual polymer particles (1) is on average larger than the adhesion energy of the individual polymer particles (1), and the polymer particles (1) in the second mixing event are stirred at a lower speed than in the first mixing event. The different speeds effect a fluidization of the polymer particles (1), which prevents a clumping of the polymer particles (1) during the mixing event. The absorbent polymers thus produced are distinguished by a particularly rapid swelling behavior.

Technology is still needed for treatment of large scale livestock operations and operations where dry stalls are not used. All references cited herein are incorporated by reference ion their entirety.

SUMMARY OF THE INVENTION

A method moderates an agricultural, farm environment in an facility where animal wastes are collected from a large scale animal housing environment into a fluid containing compartment. The fluid containing department may be located directly under the animal housing, or may have ducts that carry liquid waste away to the containment compartment. In the latter case, it is particularly useful to have some additional liquid (besides the animal waste) assist in carrying the primary liquid animal waste (and any solids) towards the containment compartment. The general type of method may involve:

a) collecting primary animal waste (e.g., feces and/or urine) from multiple animals within an animal storage facility into a fluid containing compartment. Typically the primary animal waste generates or provides in or above the fluid containing compartment at least one secondary waste selected from the group consisting of carbon dioxide, hydrogen sulfide, ammonia, mercaptans and organic acids, as well as carrying microorganisms. To address many of the problems that occur in or result from the secondary waste, a combination of i) a polymer capable of absorbing at least ten times its weight in water and ii) iodide, iodine and/or a combination of salts that react to liberate $I_2$ are provided directly into the primary waste. The addition of the combination, provided before primary waste delivery, during primary waste delivery or in a reasonable time frame (within days or weeks, so long term effects do not occur) after primary waste delivery effects flocculation of an at least one secondary waste with free iodine or liberated $I_2$ to form a flocculent.

The flocculent can be applied to agricultural farm land with significant positive benefits. As the iodine is a strong antimicrobial, the flocculent is not carrying dangerous infectious content into the soil. Of equal importance is the fact that by stably binding or sequestering available nitrogen compounds (e.g., ammonia), carbon compounds (carbon dioxide), sulfur compounds, phosphorous compounds and potassium compounds enables the flocculent to become a full value NPK (nitrogen, phosphorous and potassium) fertilizer. Thus, a dangerous waste that was a difficult disposal problem is converted to a valuable commodity. Practice of this technology can therefore strengthen a healthful environment for the animals and workers and reduce ancillary agricultural costs by providing useful fertilizer for farms as opposed to relatively toxic and odorous wastes.

The invention also provides, as a final product in the environmental moderation of the animal habitat or storage area a flocculent for use as an improved anti-leaching fertilizer and soil hydration amendment. The flocculent may have: i) a superabsorbent polymer, ii) water of hydration and iii) a residue of salts that have previously reacted to liberate $I_2$. At least some iodide is entrapped in the flocculent with the polymer. At least some iodide is in the flocculent sequestering a waste material selected from the group consisting of carbon dioxide, hydrogen sulfide, ammonia, nitrates, nitrites, methane, mercaptans and organic acids. The different waste materials may be in various states or degrees of oxidation.

DETAILED DESCRIPTION OF THE INVENTION

The present technology provides a wide range of safe and green technology to a field in need of environmental improvement, the corporate livestock system. In that system, large numbers of livestock (avian and mammals) are provided in concentrated areas that generate large volumes of animal waste. The waste provides a multiplicity of problems with respect to offensive odors, microbial concentrations, disposal problems, costs, efficiency and general health hazards for the livestock and workers. Any improvement in the environment of the system would be significant. The present technology provides a significant and major improvement to all aspects of the problem.

The present technology may also be broadly described as providing an absorbent, especially superabsorbent polymer with increased ionic sites (especially halide sites, and more particularly chlorine, bromine and iodine sites, most particularly iodine and iodide sites on the superabsorbent polymer.

Superabsorbent polymers are generally made of a polymer network and can absorb large amounts of water due to their ionic nature and interconnected structure. This network creates a membrane that allows water diffusion. The polymer absorbs water by osmosis: The large concentration of sodium inside the polymer network makes water flow into the polymer until equilibrium is reached, or the concentration of ions in the polymer equals the concentration of ions outside the polymer. (From a biological point of view, the polymer is hypertonic relative to the outside environment, which is hypotonic. Therefore, water diffuses into the polymer until equilibrium is reached.) Water is caught and held inside the polymer network by hydrogen bonds that it forms with the sodium acrylate monomers, forming a gel. Sodium polyacrylate can absorb about 800 times its weight in distilled water (800 g water:1 g polymer) and 300 times its weight in tap water. Absorbency decreases as the water's ion concentration increases. In diapers, the polymer's absorbency is only 30 times its weight due to urine's salt concentration (0.9% NaCl [aq]) plus the mechanical pressure from a baby's weight.

By the addition of the additional active ionic sites directly into the superabsorbent polymer (e.g., in initial concentrations of at least about 0.0001% by weight iodine (or other halogen)/SAP solids (excluding water weight), preferably at least 0.0005%, more preferably 0.001% by weight iodine/SAP and most preferably from 0.001% to 0.5% iodine/SAP is extremely beneficial in the practice of the present technology. No "free iodine" would be bound directly by the polymer if iodine solids were added to the SAP, but there could be a reaction used to convert the iodine to iodide or iodophors and reform iodine to enable the antimicrobial activity. This is too complex for only commercial and economis reasons, while the use of Curpidyne™ particle technology is simpler and more effective. In fact, the BASF patents mentioned earlier teach that iodine stocked on polyvinyl pyrrholidone is either iodophor, or metaliic iodine (as tri-iodide), so that a pH lowering agent like citric acid must also be present to elute the free iodine. Then, of course, the disinfectant properties are equally pH lowering besides the oxidation by iodine.

Supplemental stabilization techniques for the composition before, during or after activation within the collection area includes the acidification of the iodine that is generated by the reaction.

3. Stable Iodine Liquid Compositions/Solutions (Ready to Use and Concentrate)

An iodine solution (as generated herein) is acidified by the addition of an acid that (alone) produces a pH of less than 6.7 at 1.0 N in deionized water and preferably less than 6.5 under those parameters. Typical acids may be organic acids, inorganic acids, Lewis acids, HCl, HI, HBr (halogenic acids), $HNO_3$, $HClO_4$, $H_2SO_4$, $H_2SO_3$, and especially the family of sulfamic acids.

The iodine environment can be provided in numerous and varied tasks and services and even in combination with other additives such as stable active solutions or film-breaking compositions such as acids (e.g., sulfamic acid, hydrochloric acid, sulfuric acid, enzymes, etc.). At present, the most widely known and accepted acidizing agents include HCl, sulfamic acid, lactic acid, citric acid, and acetic acid, all with varying degrees of reactivity for descaling. The effect of acidizing with iodine gas in solution, however, also attends with additive antimicrobial effects, and when the acidized iodine is combined with sulfamic acid, a powerful and effective method is provided for dissolving and remediating biofilms, and chelating heavy metals which may be solubilized by the process, or otherwise contained in water, especially after physical disruption as described herein. The acid may be present in any amount desired, with an amount that is at least 0.01N in the aqueous environment being desirable.

The solution is preferred where the acid comprises a sulfamic acid compound having the formula:

wherein R is independently selected from the group consisting of hydrogen and electron-withdrawing groups. The acid may comprise a sulfamic acid compound having the formula:

wherein R is independently selected from the group consisting of hydrogen, halogen, cyano, C1-C6 alkyl, C1 to C6 substituted alkyl, perhalo alkyl, halosubstituted alkyl, and electron-withdrawing groups.

The solution may have at least one R is hydrogen in the sulfamic acid compound or only and exactly one R is hydrogen.

Sulfamic acid is also a primitive surfactant, and when added to free iodine in water and stabilized by varying added compounds such as silicates (e.g., sodium metasilicate) and phosphates and sulfonates (e.g., sodium xylene sulfonate or phosphate), yields a disinfecting and biofilm removing detergent compound which is active within the technologies described herein for oilfield or watershed applications as a single formulary product. The term a "sulfamic acid compound" or a member of the family of sulfamic acids or class of sulfamic acids is herein defined as any sulfamic acid central moiety with a single substituent on the amide group of the sulfamic acid moiety or sulfamic acid core structure that still allows the sulfamic acid derivative in the family of sulfamic acids to display a pH of less than 6.8 at 0.5N in deionized water, preferably less than 6.5 under those parameters (e.g., 5.5 to 6.7, 5.5 to 6.2, and 4.0-6.7, and 3.0 to 6.7 and even lower levels of acidity up to 6.5, up to 6.6 or up to 6.7 pH). As non-limiting examples of these known sulfamic acid family compounds are sulfamic acid, iodosulfamic acid, chlorosulfamic acid, bromosulfamic acid, fluorosulfamic acid, alkylsulfamic acid (with C1-C8 carbon groups, whether linear, branched or cyclic, such as cycloheylsulfamic acid, and substituted or not, such as trifluoromethylsulfamic acid, pentachloroethylsulfamic acid, etc.), cyanosulfamic acid, any electron-withdrawing group on the amide position of the sulfamic acid and even lightly electron-donating groups that do not change the sulfamic acid from an acid to a base at 1.0N in deionized water.

The formula for sulfamic acid is $NH_2SO_3H$ and the corresponding formula for a sulfamic acid compound is represented by:

$NR_2SO_3H$, wherein R is independently selected from the groups described above, such as hydrogen, halogen, cyano, C1-C6 alkyl or substituted alkyl, perhalo alkyl, halosubstituted alkyl, electron-withdrawing groups, mild electron-donating groups and the like. It is preferred that at least one R group is hydrogen.

The inventor has noted that the addition of sulfamic acid (in particular) to all CupriDyne™ treatment composition formulas can provide ultimate stability or even enhanced activity in its various antimicrobial or surface treatment procedures. The sulfamic acid is both an acidifying agent (and other acids may be used) and a primitive surfactant. CupriDyne™ antimicrobial compositions in water is stabilized (free iodine is continuously available) by lowering pH to 5.5-6.7. Even the CuI resulting component is held in solution. The addition of surfactants, such as sodium metasilicate and sodium tripolyphosphate assists in completing a detergent preparation formula.

These solutions are antimicrobial, have antiodor effects, and can bleach or remove some stains.

The flash antimicrobial effect of free iodine is still unique, because in the process of making an iodide somewhere along the polymer chain, there is an active and effective oxidation step. The SAP's we use are normally cationic, so many of the reaction products are electrically bound to the polymer. The combination of the iodine with the SAP and the Cu with the SAP and the combination of both the iodine and the Cu with the SAP acts to provide a platform (the modified polymer) that creates a hypertonic superabsorbent polymer. The polymer, with the entrained iodine, iodide and copper can act as a chelate or chlathrate while performing its other functions of antimicrobial and anti-odor activities. In addition to these functions, the coagulated or flocculated mass of the liquid animal waste and the hypertonic SAP can be then directly added (with or without any intermediate drying) as a fertilizer onto arable land. It may even be added safely to landfill mass to improve the quality of the fill.

It is to be noted that the iodine less preferably may be added into the SAP even in a dry state, rather than using the Cupridyne™ technology to release it upon demand, mainly because of the high moisture content and the duration of the presence of the iodine/SAP combination in the liquid waste. Therefore, although it is highly preferred to provide the iodine-releasing system as the Cupridyne™ system or pellets, any other method of providing the additional halogen (iodine or iodide) content and subsequent ionic sites into the superabsorbent polymers, especially in combination with the copper and other counter-anions.

A method according to the present technology moderates an environment in an area where animal wastes are collected in a fluid containing compartment. The fluid containing compartments receive solid, liquid and mixed solid and liquid wastes from large numbers of livestock (e.g., each compartment receives waste from at least ten animals). The method acts by:

a) collecting the animal waste in a fluid containing compartment, the animal waste generated or provided in or above the fluid containing compartment, and at least one waste selected from the group consisting of carbon dioxide, hydrogen sulfide, ammonia, methane, mercaptans and organic acids (the gases may be dissolved in the solids or liquids or may be provided by decomposition of or reaction of the solid and liquid wastes);

b) providing a combination of i) a polymer capable of absorbing at least ten times its weight in water and ii) a combination of salts that react to liberate $I_2$; and c) flocculating an at least one waste with liberated $I_2$ to form a flocculant.

The preferred salts are disclosed in the Code Applications and Patents cited above and include a combination of salts comprising cupric sulfate and potassium iodide. The polymer may provide a hypertonic polymer when combined with ions from the combination of salts. A preferred polymer comprises acrylic acid, methacrylic acid, acrylic acid salt and/or methacrylic acid salt moieties. A most preferred polymer comprises a superabsorbent polymer as known in the art and as described herein. These superabsorbent polymers include materials that absorb at least 10×, at least 20×, at least 40× and at least 100× times their solids weight of water.

The fluid containment compartment is generally positioned below ground and animal waste from animal housing is fed by gravity or siphoned or periodically lightly flushed from the animal housing into the fluid containment compartment. An aspect of the present technology that has not been considered in the art is the interaction and synergy of the salt system releasing iodine and the superabsorbent polymer. At least the iodine (as molecular iodine and resulting iodide) can attach to moieties in the polymer to create iodine and/or iodide reactive sites and functions on the polymer molecule. The hydrated polymer (superabsorbent polymer) therefore provides sites that can sequester other molecules and/or provide antimicrobial activity. The cupric rich and iodine rich polymer composition can and does cause flocculation of the animal waste materials, sequesters carbon dioxide (each $I_2$ molecule can sequester approximately 14 carbon dioxide molecules), bind or sequester nitrogen containing compounds (ammonia, amines, etc.), bind or sequester mercaptans and sulfur compounds, and fix those compounds within the flocculation so that there are biologically available and retained in the flocculent when it is applied to soil as fertilizer. The totality of these abilities was not known prior to the present invention.

The method is particularly beneficial in providing secondary fertilizer from the process when at least one waste is ammonia and the iodine binds ammonia into the polymer and the flocculant is removed from the fluid containment container and spread onto soil to provide agriculturally available nitrogen compounds for plant fertilizer.

Similarly, the method is particularly beneficial in providing secondary fertilizer from the process when at least one waste is carbon dioxide and the iodine binds the carbon dioxide into the polymer and the flocculant is removed from the fluid containment container and spread onto soil to provide agriculturally available carbon-based compounds for plant fertilizer. By sequestering carbon dioxide, those specific greenhouse emissions are reduced from the corporate scale livestock production and returned to the ecosystem in a non-greenhouse gas composition.

Superabsorbent polymers (SAP) (also called slush powder) are polymers that can absorb and retain extremely large amounts of a liquid relative to their own mass.

Water absorbing polymers, classified as hydrogels, absorb aqueous solutions through hydrogen bonding with the water molecule. So an SAP's ability to absorb water is a factor of the ionic concentration of an aqueous solution. In deionized and distilled water, SAP may absorb 500 times its weight (from 30-60 times its own volume), but when put into a 0.9% saline solution, the absorbency drops to maybe 50 times its weight. The presence of valent cations in the solution will impede the polymers ability to bond with the water molecule.

The total absorbency and swelling capacity are controlled by the type and degree of cross-linking to the polymer. Low density cross-linked SAP generally has a higher absorbent capacity and swell to a larger degree. These types of SAPs also have a softer and more cohesive gel formation. High cross-link density polymers exhibit lower absorbent capacity and swell. The gel strength is firmer and can maintain particle shape even under modest pressure.

In the early 1960s, the United States Department of Agriculture (USDA) was conducting work on materials to improve water conservation in soils. They developed a resin based on the grafting of acrylonitrile polymer onto the backbone of starch molecules (i.e., starch-grafting). The hydrolyzed product of the hydrolysis of this starch-acrylonitrile co-polymer gave water absorption greater than 400 times its weight. Also, the gel did not release liquid water the way that fiber-based absorbents do.

The polymer came to be known as "Super Slurper." The USDA gave the technical know how to several USA companies for further development of the basic technology. A wide range of grating combinations were attempted including work with acrylic acid, acrylamide and polyvinyl alcohol (PVA). Polyacrylate/polyacrylamide copolymers were originally designed for use in conditions with high electrolyte/mineral content and a need for long term stability including numerous wet/dry cycles. Uses include agricultural and horticultural. With the added strength of the acrylamide monomer, used as medical spill control, wire & cable waterblocking.

Copolymer Chemistry

Superabsorbent polymers are now commonly made from the polymerization of acrylic acid blended with sodium hydroxide in the presence of an intiator to form a poly-acrylic acid sodium salt (sometimes referred to as sodium polyacrylate). This polymer is the most common type of SAP made in the world today. Other materials are also used to make a superabsorbent polymer, such as polyacrylamide copolymer, ethylene maleic anhydride copolymer, cross-linked carboxymethyl-cellulose, polyvinyl alcohol copolymers, cross-linked polyethylene oxide, and starch grafted copolymer of polyacrylonitrile to name a few. The latter is one of the oldest SAP forms created.

Today superabsorbent polymers are made using one of two primary methods; suspension polymerization or solution polymerization. Both processes have their advantages over the other and both yield a consistent quality of product.

Solution Polymerization

Solution polymers offer the absorbency of a granular polymer supplied in solution form. Solutions and can be diluted with water prior to application. After drying at a specific temperature for a specific time, the result is a coated substrate with superabsorbent functionality. For example, this chemistry can be applied directly onto wires & cables, though it is especially optimized for use on components such as rolled goods or sheeted substrates.

Solution based polymerization is the most common process used today for SAP manufacture. This process is efficient and generally has a lower capital cost base. The solution process uses a water based monomer solution to produce a mass of reactant polymerized gel. The polymerization's own reaction energy (exothermic) is used to drive much of the process, helping reduce manufacturing cost. The reactant polymer gel is then chopped, dried and ground to its final granule size. Any treatments to enhance performance characteristics of the SAP are usually accomplished after the final granule size is created.

Suspension Polymerization

The suspension process is practiced by only a few companies because it offers a higher degree of production control and product engineering during polymerization step. This process suspends the water based reactant in a hydrocarbon based solvent. The net result is that the suspension polymerization creates the primary polymer particle in the reactor rather than mechanically in post-reactions stages. Performance enhancements can also be during or just after the reaction stage.

Many industrial companies produce some type of superabsorbent polymer. In the U.S., current manufacturers of acrylate-based superabsorbents include The Dow Chemical Company, Sanyo Chemical Industries, Nippon Shokubai Company, and the Chemdal Corporation, which is a subsidiary of AMCOL International. Other manufacturers located in Europe include AMCOL, Stockhausen GMBH, Dow Chemical, Hoechst Casella, Allied Colloids, and Nippon Shokubai. Superabsorbent polymer production in Japan comes from companies such as Nippon Shokubai, Sanyo, Mitsubishi Petrochemical Company, and Sumitomo Seika.

The structure of Polyacrylic acid is as follows, and contains an ionizable group on each repeat unit (—COOH).

wherein n is an integer.

These polymer chains are then crosslinked at the —OH. The mechanism of swelling of ionized, crosslinked polymer networks is based upon the concept of osmotic pressure. The polymer acts as a semipermeable membrane which does not allow charge substituents to exit the polymer into the surrounding solution. This is because the ionized monomeric units contain fixed charges which attract and fix ions from the outer solution. Therefore, a charge gradient is set up, in which the concentration of free ions is greater outside of the polymer. Therefore, the osmotic pressure exerted by the gradient causes the polymer chain to swell as further ions diffuse in.

EXAMPLES 1. (Prophetic) 10 kilogram of superabsorbent polymer (such as that available from Jinhu Sanitary Napkin Equipment Co. Ltd., Taiwan, China, called SAP—Superabsorbent Polymer, model number 283FHA) in fiber form would be combined by dry mixing with 200 grams each of cupric sulfate particles and potassium iodide particles having silica standoff particles surrounding the potassium iodide particles according to the teachings of Published U.S. Patent Documents 20090028915; 20090193562; 20090145391. The approximately stoichiometric provision of cupric sulfate particles and potassium iodide particles is known from these references and in the art as a Cupridyne™ system, from BioLargo, Inc.

The dry blend would be carried to a pig-under commercial pen system having 150 swine billeted in the facility. The dry blend would be evenly distributed on the floor of the holding tank before swine were stabled for long term feeding and growth in the facility. As wastes from the swine pass through the open flooring to the pig-under waste collection compartment, the liquid content in the waste would begin to open up the KI particles and allow generation of iodine. The iodine would be in an active antimicrobial state, even though binding into the superabsorbent polymer. The iodine would sequester ammonia, organic acids and carbon dioxide in or generated in the waste, while also killing microbes in the collecting waste. This action would reduce levels of infectious materials and reduce odors in the penning system.

After about three months, the wastes would have fully exhausted the absorption, flocculation and antimicrobial activity of the iodine, so the flocculent would be carried to the fields for dispersal. The iodine and iodide have bound the ammonia, carbon dioxide and organic acids into the superabsorbent polymer to enable the flocculent to fix the nutrients to the soil. The SAP would then degrade over time as th nutrients were used up by planting in the field.

Summary

Liquid swine manure was treated by physical-chemical treatment, including coagulation and flocculation, followed by sedimentation at bench scale level. CupriDyne™ superabsorbent polymer (SAP) and CupriDyne™ tablets were used as coagulant and disinfectant agents, respectively, applied at different phases. The optimum conditions were determined based on the removal of total suspended solids (TSS) for Phase 1, and ammonia and total organic carbon (TOC) reductions for Phase 2. It was found that SAP at concentration of 1.25 g/L was able to reduce 33% of the initial TSS, in experiments using supernatant at natural pH. Following the SAP application, 80% of initial ammonia, 78% of initial TOC, and 93% of the total coliforms were reduced using 40 mg/L of free iodine. Experiments were also performed using diluted supernatant. The results indicated that SAP at concentration of 0.5 g/L was capable of reducing 82% of the initial TSS in experiments using supernatant, diluted 5 times, at pH 11. After the tablet application, 50% of initial ammonia, 77% of initial TOC, and 100% of the total coliforms were reduced using 80 mg/L of free iodine.

From the leaching tests using non-diluted supernatant, it was found that 24% of the chloride and 50% of the phosphate ions retained in the sludge leached to the ultrapure water after 48 hours. For the experiments using diluted supernatant, it was noted that 12% of the chloride and 2% of the nitrite ions retained in the sludge were found in the ultrapure water after 48 hours. The results obtained suggest that the CupriDyne™ system technology is a very effective alternative to existing liquid manure handling methods in terms of nutrient, TSS, and coliform reductions. Special attention should be given to the sludge generated after treatment because of a possible leaching of major ions.

The livestock industries are growing rapidly along with the human population. Because of this increasing trend, tons of swine manures are being generated annually worldwide. Swine manure contains the urine and feces of pigs, as well as water spillage, remains of undigested feed items, and antimicrobial drug residues. Swine manure may contain about 80 to 90% liquid when it is excreted. Typical swine manure is characterized by high content of solids, high biochemical oxygen demand, high phosphorus and nitrogen contents as well as high levels of microbial population. Environmental water quality problems caused by swine manure have arisen because of the excess of manure generation relative to land availability and inadequate manure storage and handling procedures. Improper management of animal waste can cause a negative impact on the environment. Problems such as water contamination and human health concerns due to the presence of microorganism in animal manures have been reported. Other problems associated with swine manure are odors caused by gases produced by decomposing manure in swine manure facilities. Nutrients leaching below the root zone and into groundwater together with nutrients entering into surface water systems through runoff from manure store facilities are other concerns caused by the improper swine manure management.

Waste animal management may comprise collection, storage, treatment and utilization. A common method to handle swine manure is wastewater treatment. Physico-chemical methods have been found to be effective technologies to remove solids and nutrients from animal manure. These methods are used to separate liquid and solid fractions for better management, to reuse the liquids, and to reduce the volume of manure to be transported. The separation of this wastewater may include chemical-aid coagulation, mixing, flocculation, and sedimentation. Chemicals coagulants used in chemical treatment include inorganic chemicals such as alum and ferric salts and organic substances such as polyamines and polyquaternary amines Coagulation-flocculation is a conventional physical-chemical treatment process used to separate the suspended solids portion from the water. The objectives of this research were to investigate whether the coagulation-flocculation process utilizing a new mineral and salt formulation called CupriDyne™ system was an effective and applicable process for the treatment of swine manure and to find the optimum treatment conditions and most effective chemical doses to yield the higher removal efficiencies in terms of total suspended solids and nutrient removal. To assess the safety for disposal of sludge generated from the coagulation/flocculation process, a leaching study was conducted as the last goal of this research.

Research on these issues was performed by the inventor and results were achieved through the performance of the series of phases listed and discussed below.

Phase 1: The determination of optimum conditions based on maximum total suspended solids removal during coagulation and flocculation was the first step in this research. The experiments were performed using the classic jar test apparatus (Phipps and Bird 6-place paddle stirrer apparatus). In this stage, the CupriDyne™ system plus superabsorbent polymer (SAP) was added to the process as coagulant agent. The Cupridyne™ would be tried at various times in weight ranges of from 0.001% by weight of the two reactive ingredients (stoichiometric, 1:1, molecular ratio of $CuSO_4$ and KI particles), up to 50% by weight of the active ingredients in small laboratory scale tests to see if flocculation could occur. Tablet applications (weight to weight of the dry SAP) of from 0.01% to 10% were found to be commercially viable, with greater amounts of the pellets having good effect, but deemphasizing the flocculation function, while lesser amounts would not have either as immediate large scale effect or as persistent an effect as the intermediate ranges. All ranges of combined Cupridyne™ pellets and SAP between 0.001% to 50% showed measurable benefits according to the present technology and are including within the broad scope of this disclosure. The most important parameters affecting the coagulation/flocculation processes such as coagulation mixing intensity, coagulation mixing time, coagulant dose were determined. During the experiments, the raw and treated liquid swine manure were characterized by various water quality parameters including pH, total suspended solids (TSS), total volatile solids (TVS), total fixed solids (TFS), total dissolved solids (TDS), total phosphorus (TP), total Kjeldahl nitrogen (TKN), nitrite, nitrate, biochemical oxygen demand (BOD), and chemical oxygen demand (COD).

The CupriDyne™ system technology generates free iodine by dissolving two proprietary chemical compounds in water (stoichiometric, 1:1, molecular ratio of $CuSO_4$ and KI particles). Free iodine is an effective disinfectant and is soluble in water up to 337 mg/L. Therefore, to test the disinfection efficiency, fecal and total coliform were determined before and after treatment. The toxicity of the untreated and treated samples was assessed by using the Microtox® bioassay.

Phase 2: The supernatant generated during coagulation/flocculation treatment under the optimum conditions was used in the next step in this research. The supernatant was treated using CupriDyne™ system tablets (stoichiometric, 1:1, molecular ratio of $CuSO_4$ and KI particles) as oxidizing agent by generating iodine in water. The optimum conditions were determined based on the maximum total organic carbon (TOC) and ammonia ($NH_3$) removal. In this stage, the water quality parameters mentioned in Phase 1 were also determined.

Phase 3: The sludge generated from coagulation/flocculation under optimum conditions was used in a leaching test. The sludge was dried and then washed with clean water. After a certain period of contact with the dried sludge, the water was collected and analyzed to test the leaching of nutrients and other elements.

Results and Discussions

Swine manure characteristics vary significantly depending on the several factors, including water consumption, on-site operation, seasonal conditions, and waste handing methods, among others. Table 1 summarizes the characteristics of the primary settled swine manure.

Preliminary Settling

Preliminary settling has been described as an effective and economic liquid manure treatment processes. In this study, the raw fresh swine manure wastewater was allowed to settle prior to any treatment. It was found that the initial TSS decreased a 38% after 2.5 hours and 66% after 19 days of settling, as displayed in FIG. 1.

Figure 1:
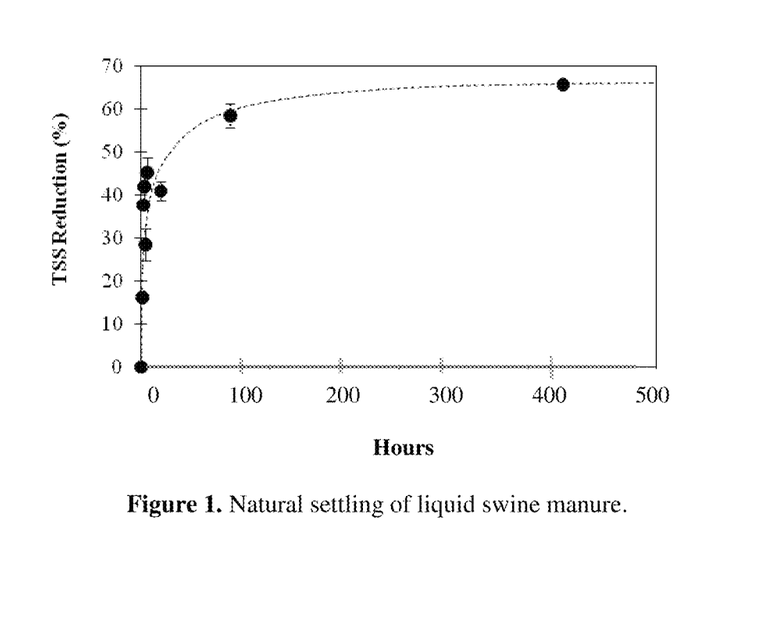
FIG. 1—Graph. Natural settling of liquid swine manure. Determination of Speed and Mixing Time.

FIG. 1. Natural settling of liquid swine manure.

Determination of Speed and Mixing Time

Figure 2:
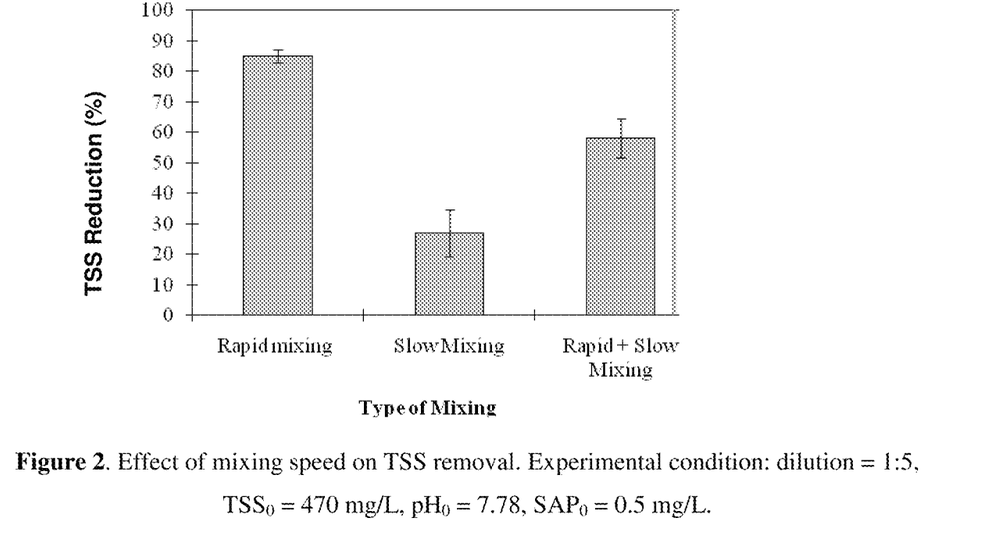
FIG. 2—Graph. Effect of mixing speed on TSS removal. Experimental condition: dilution=1:5, $TSS_0$=470 mg/L, $pH_0$=7.78, $SAP_0$=0.5 mg/L.
Figure 3:
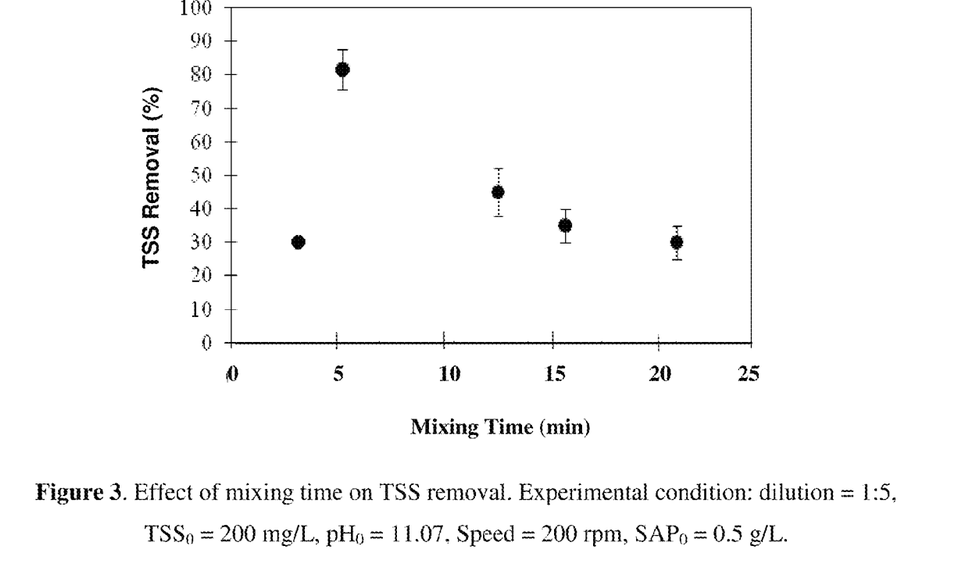
FIG. 3—Graph. Effect of mixing time on TSS removal. Experimental condition: dilution=1:5, $TSS_0$=200 mg/L, $pH_0$=11.07, Speed=200 rpm, $SAP_0$=0.5 g/L FIG. 4—Graph. TSS removal using supernatant without dilution. Experimental conditions: $TSS_0$=2300 mg/L, $pH_0$=7.36, speed: 200 rpm, mixing time=5 min. Similar tests were conducted using supernatant diluted 5 times.

It has been found that the most important factors affecting the performance of coagulation/flocculation process are: (1) water pH; (2) coagulation mixing intensity; (3) coagulation mixing time; (4) coagulant dose; (5) type of coagulant; (6) type of coagulant aid; (7) and dose of coagulant aid; (8) flocculation mixing intensity; and (9) flocculation time. From the preliminary test results, it was found that jar test performed at 200 rpm gave the maximum TSS removal using swine manure supernatant, diluted 5 times (FIG. 2). It was also fund that the combination of slow mixing and rapid mixing reported the lower TSS removal. FIG. 3 shows the effect of mixing time on the TSS removals. The results indicated that 81.6% of TSS was depleted using 5 minutes of rapid mixing at 200 rpm. Based on these results, the optimization of Phase 1 and Phase 2 were performed using 5 minutes of rapid mixing at 200 rpm.

FIG. 2. Effect of mixing speed on TSS removal. Experimental condition: dilution=1:5, $TSS_0$=470 mg/L, $pH_0$=7.78, $SAP_0$=0.5 mg/L.

FIG. 3. Effect of mixing time on TSS removal. Experimental condition: dilution=1:5, $TSS_0$=200 mg/L, $pH_0$=11.07, Speed=200 rpm, $SAP_0$=0.5 g/L Determination of Optimum Conditions Phase 1

The Phase 1 considered the use of CupriDyne™ superabsorbent polymer (SAP). The determination of optimum conditions was based on maximum total suspended solids removal during coagulation and flocculation. Different dilutions (1:1, 1:3, and 1:5 Cupridyne™ tablets to dry weight SAP) and pHs were tested to optimize the TSS removal. It was found the optimum TSS removal (32.8%) was achieved using 1.25 g/L SAP at pH 7.36, in experiments performed using supernatant without dilution (FIG. 4).

Figure 4:
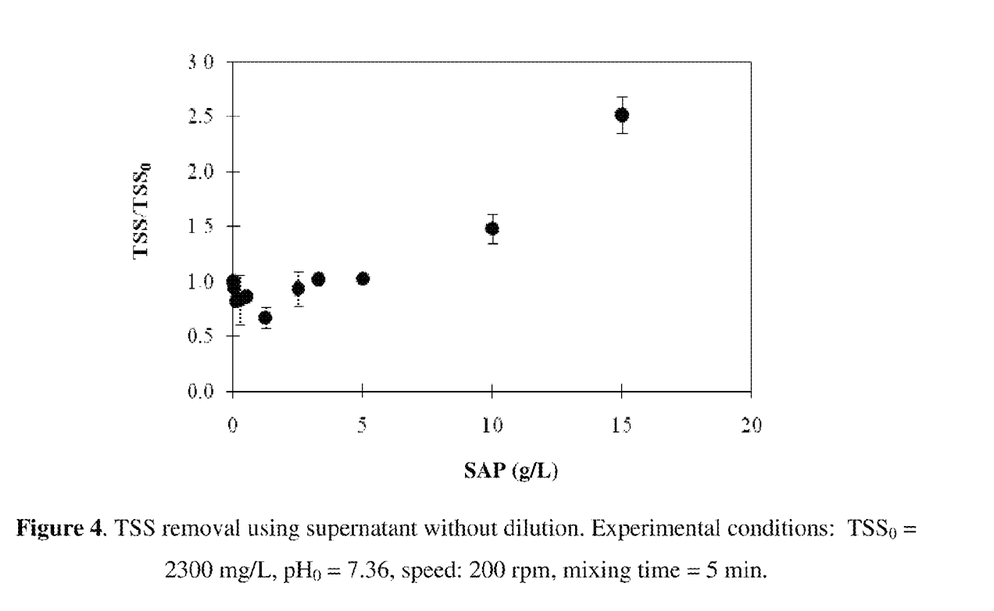

FIG. 4. TSS removal using supernatant without dilution. Experimental conditions: $TSS_0$=2300 mg/L, $pH_0$=7.36, speed: 200 rpm, mixing time=5 min. Similar tests were conducted using supernatant diluted 5 times. As displayed in FIG. 5, an 81.64% of the initial TSS was removed using 0.5 g/L SAP at pH 11. At natural pH, removals of 50.2% were recorded using 0.5 g/L SAP.

Figure 5:
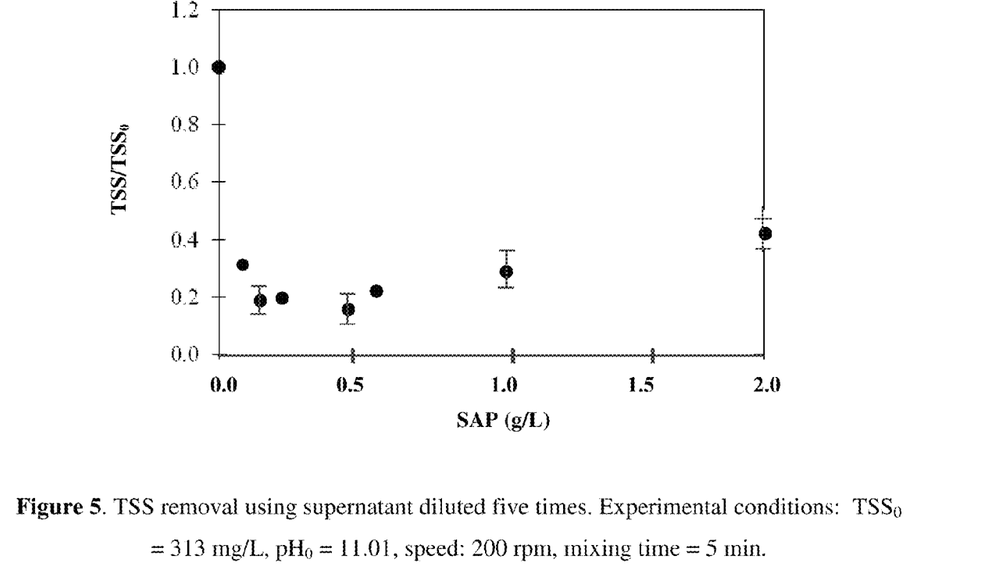
FIG. 5—Graph. TSS removal using supernatant diluted five times. Experimental conditions: $TSS_0$=313 mg/L, $pH_0$=11.01, speed: 200 rpm, mixing time=5 min.

FIG. 5. TSS removal using supernatant diluted five times. Experimental conditions: $TSS_0$=313 mg/L, $pH_0$=11.01, speed: 200 rpm, mixing time=5 min.

Determination of Optimum Conditions Phase 2

Figure 6:
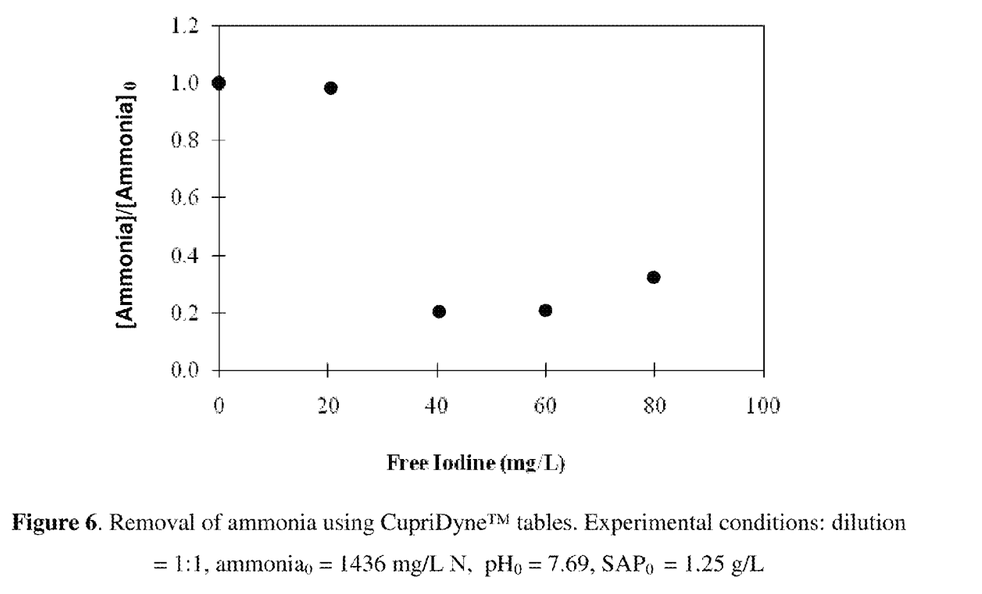
FIG. 6—Graph. Removal of ammonia using CupriDyne™ tables. Experimental conditions: dilution=1:1, $ammonia_0$=1436 mg/L N, $pH_0$=7.69, $SAP_0$=1.25 g/L FIG. 7—Graph. TOC Removal using CupriDyne™ tables. Experimental conditions: dilution=1:1, $TOC_0$=1732 mg/L C, $pH_0$=7.69, $SAP_0$=1.25 g/L.
Figure 7:
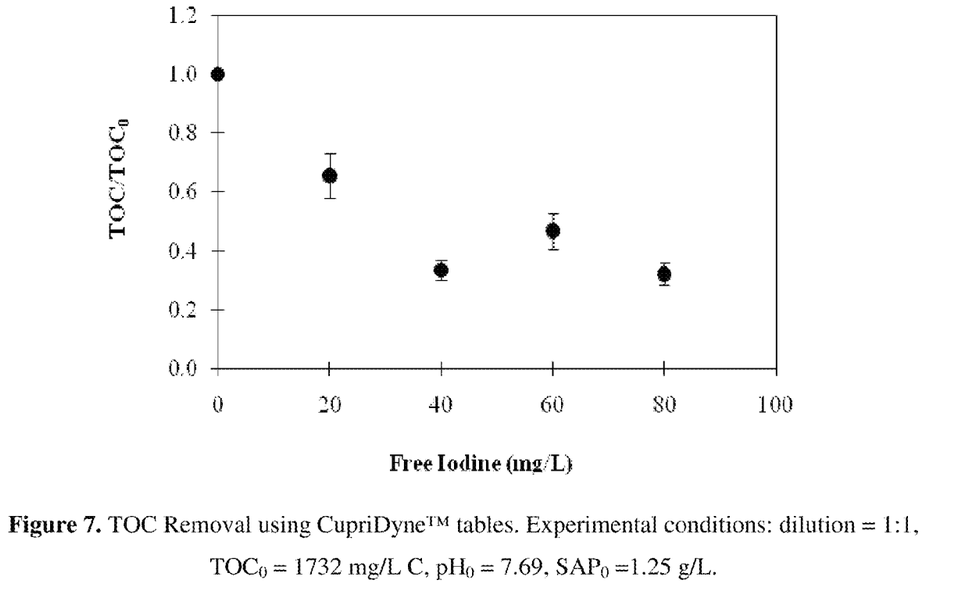

The treated supernatant generated during coagulation/flocculation treatment under the optimum conditions was used in Phase 2. The supernatant was treated using CupriDyne™ system tablets as oxidizing agent. The optimum conditions were determined based on the maximum total organic carbon (TOC) and ammonia ($NH_3$) removal. From the experiments using supernatant without dilution, it was found a removal of 80% ammonia (initial concentration of 1486 mg/L N) using 40 mg/L of free iodine, as shown in FIG. 6. Under the same conditions, the TOC levels decreased a 78% (FIG. 7). Similar tests were performed using the diluted supernatant at pH 11. The results indicated a removal of 50% ammonia (initial concentration of 325 mg/L N) using 80 mg/L of free iodine, as displayed in FIG. 8. Under the same conditions, the TOC levels decreased a 77% (FIG. 9).

FIG. 6. Removal of ammonia using CupriDyne™ tables. Experimental conditions: dilution=1:1, $ammonia_0$=1436 mg/L N, $pH_0$=7.69, $SAP_0$=1.25 g/L FIG. 7. TOC Removal using CupriDyne™ tables. Experimental conditions: dilution=1:1, $TOC_0$=1732 mg/L C, $pH_0$=7.69, $SAP_0$=1.25 g/L.

Figure 8:
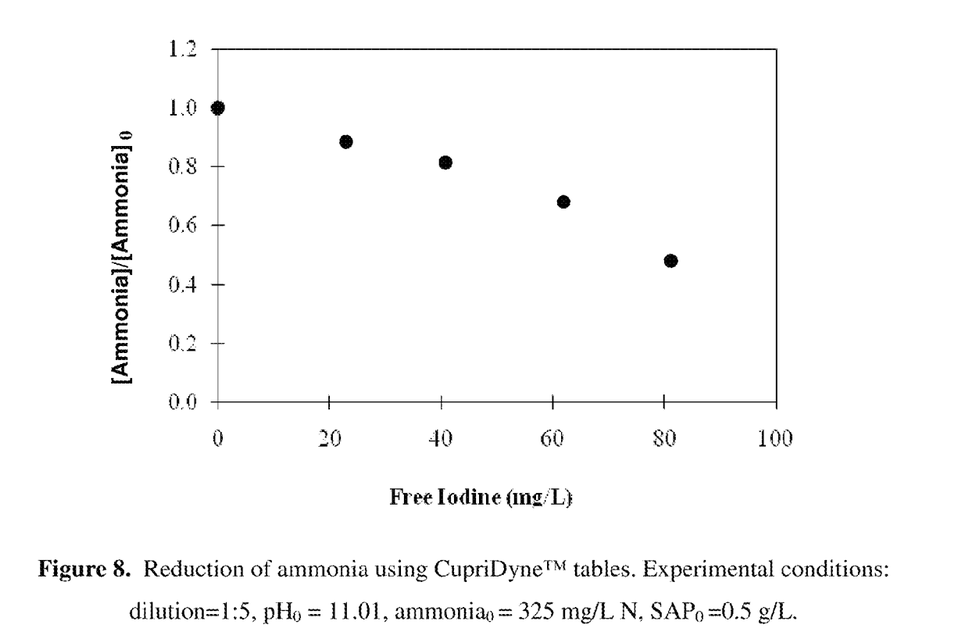
FIG. 8—Graph. Reduction of ammonia using CupriDyne™ tables. Experimental conditions: dilution=1:5, $pH_0$=11.01, $ammonia_0$=325 mg/L N, $SAP_0$=0.5 g/L.

FIG. 8. Reduction of ammonia using CupriDyne™ tables. Experimental conditions: dilution=1:5, $pH_0$=11.01, $ammonia_0$=325 mg/L N, $SAP_0$=0.5 g/L.

Figure 9:
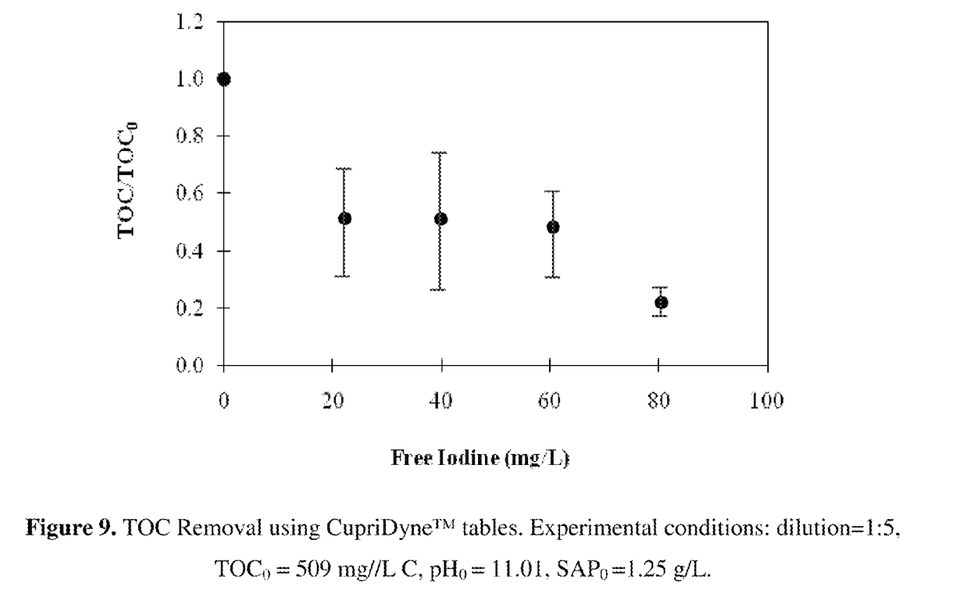
FIG. 9—Graph. TOC Removal using CupriDyne™ tables. Experimental conditions: dilution=1:5, $TOC_0$=509 mg/L C, $pH_0$=11.01, $SAP_0$=1.25 g/L.

FIG. 9. TOC Removal using CupriDyne™ tables. Experimental conditions: dilution=1:5, $TOC_0$=509 mg/L C, $pH_0$=11.01, $SAP_0$=1.25 g/L.

Toxicity Analysis

Figure 10:
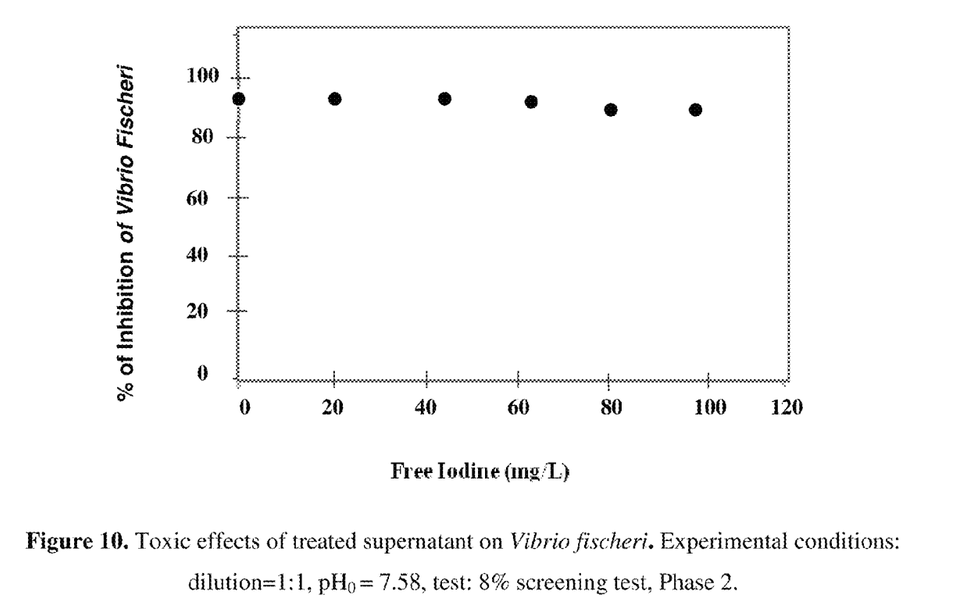
FIG. 10—Graph. Toxic effects of treated supernatant on *Vibrio fischeri*. Experimental conditions: dilution=1:1, $pH_0$=7.58, test: 8% screening test, Phase 2.

The acute toxicity of samples before and after treatments was measured using the Microtox® bioassay. A model 500 Microtox® analyzer (Strategic Diagnostic Inc.) was used to measure the light emitted by the photobacterium. Microtox® 8% screening test protocol was used for the toxicity assessment of samples. The toxicity analysis was performed within 24 h after treatment and using 8% the initial sample concentrations. Positive controls for the Microtox® assay were carried out using phenol standards. As illustrated in FIG. 10, the acute toxicity was evaluated using different free iodine concentrations (after Phase 2). The toxicity of the untreated samples was found to inhibit the 93% of the photobacterium. It was noted a decrease of the toxicity (inhibition) with increasing iodine concentrations. An inhibition of 92% was observed using 40 mg/L free iodine in experiments using non-diluted supernatant.

For experiments using diluted supernatant, an increment of the *Vibrio fischeri* inhibition was observed with increasing free iodine levels. Control tests were conducted using free iodine solution in ultrapure water. It was found that free iodine was able reduce the luminescent bacteria, showing his effectiveness as disinfectant.

FIG. 10. Toxic effects of treated supernatant on *Vibrio fischeri*. Experimental conditions: dilution=1:1, $pH_0$=7.58, test: 8% screening test, Phase 2.

Other experimentation was done in an Eight Percent Screening Test of diluted supernatant. Experimental condition: dilution 1:5, $pH_0$=11.02, Phase 2.

Summary of Results Phase 1 and Phase 2

Tales 2 and 3 show a summary of the characteristics of the supernatant and diluted supernatant after Phase 1 (SAP) and Phase 2 (Tablets).

TABLE 2

Characteristics of supernatant before and after treatment.

| Parameter | Raw Supernatant | After Phase 1 | After Phase 2 |
|---|---|---|---|
| TSS (mg/L) | 1217 | 840 | 690 |
| pH | 7.69 | 7.91 | 7.98 |
| Turbidity (NTU) | 459 | 370 | 172 |
| TOC mg/L C | 1858 | 1732 | 580 |
| Total Phosphorous | 310 | 296 | 286 |
| Ammonia | 1662 | 1486 | 304 |
| Total Coliform (CFU/100 mL) | $1.2 \times 10_6$ | $0.1 \times 10_6$ | $0.09 \times 10_6$ |
| % inhibition on *Vibrio fischeri* | 94.00 | 92.75 | 92.06 |

TABLE 3

Characteristics of diluted supernatant before and after treatment.

| Parameter | Raw Supernatant | After Phase 1 | After Phase 2 |
|---|---|---|---|
| TSS (mg/L) | 540 | 270 | 110 |
| pH | 10.87 | 10.79 | 10.69 |
| Turbidity | 211 | 202 | 100 |
| TOC mg/L C | 599 | 509 | 118 |
| Total Phosphorous | 217 | 138 | 69 |
| Ammonia | 329 | 325 | 163 |
| Total Coliform (CFU/100 mL) | 9225 | 6150 | None detected |
| % inhibition on *Vibrio fischeri* | 65.52 | 64.69 | 90.90 |

Leaching Results

The last phase of this study was designed to investigate the leaching of nutrients and other elements from the sludge generated after coagulation/flocculation, under optimum conditions. During the leaching test, the samples were withdrawn after 1, 6, 12, 24 and 48 hours.

Tables 4, 5, 6 and 7 display the results of the leaching tests for major ions.

Page 14

TABLE 4

Major ions during leaching test after treatment of non-diluted supernatant, Phase 1.

| | Phase 1-1 hr | Phase 1-6 hr | Phase 1-12 hr | Phase 1-24 hr | Phase 1-48 hr |
|---|---|---|---|---|---|
| Anions | | | | | |
| Chloride (mg/L) | 58.7 | 73.6 | 90.5 | 101.2 | 109.8 |
| Nitrite (mg/L) | n.a. | n.a. | n.a. | n.a. | n.a. |
| Nitrate (mg/L) | n.a. | n.a. | 0.08 | 7.1 | n.a. |
| Phosphate (mg/L) | 5.4 | 7.0 | 10.0 | n.a. | 19.9 |
| Sulfate (mg/L) | 9.1 | 10.7 | 15.7 | 17.2 | 21.8 |
| Cations | | | | | |
| Sodium (mg/L) | 17.2 | 21.8 | 28.1 | 32.9 | 40.0 |
| Ammonium (mg/L) | 11.1 | 13.9 | 15.6 | 17.8 | 21.7 |
| Potassium (mg/L) | 37.4 | 47.1 | 58.4 | 66.4 | 79.9 |
| Magnesium (mg/L) | 0.1 | 0.1 | 0.4 | 0.2 | 0.2 |
| Calcium (mg/L) | 1.2 | 1.4 | 2.7 | 2.7 | 5.0 |

TABLE 5

Major ions during leaching test after treatment of non-diluted supernatant, Phase 2.

| | Phase 2-1 hr | Phase 2-6 hr | Phase 2-12 hr | Phase 2-24 hr | Phase 2-48 hr |
|---|---|---|---|---|---|
| Anions | | | | | |
| Chloride (mg/L) | 61.1 | 61.5 | 63.6 | 64.6 | 66.8 |
| Nitrite (mg/L) | n.a. | n.a. | n.a. | n.a. | n.a. |
| Nitrate (mg/L) | n.a. | n.a. | n.a. | 0.07 | 0.04 |
| Phosphate (mg/L) | 12.8 | 13.1 | 13.1 | 13.4 | 15.8 |
| Sulphate (mg/L) | 15.1 | 15.3 | 15.7 | 17.9 | 17.9 |
| Cations | | | | | |
| Sodium (mg/L) | 24.0 | 24.7 | 24.57 | 25.8 | 29.8 |
| Ammonium (mg/L) | 21.72 | 22.2 | 22.7 | 23.4 | 26.9 |
| Potassium (mg/L) | 38.4 | 39.2 | 40.2 | 42.0 | 47.2 |
| Magnesium (mg/L) | 0.6 | 0.4 | 0.47 | 0.4 | 0.5 |
| Calcium (mg/L) | 12.4 | 4.2 | 4.27 | 4.1 | 4.5 |

TABLE 6

Major ions during leaching test after treatment of diluted supernatant, Phase 1.

|  | Phase 1-1 hr | Phase 1-6 hr | Phase 1-12 hr | Phase 1-24 hr | Phase 1-48 hr |
|---|---|---|---|---|---|
| Anions |  |  |  |  |  |
| Chloride (mg/L) | 21.7 | 22.0 | 23.5 | 23.0 | 23.7 |
| Nitrite (mg/L) | n.a. | 0.02 | n.a. | 0.0109 | n.a. |
| Nitrate (mg/L) | n.a. | 0.03 | 0.07 | n.a. | 0.007 |
| Phosphate (mg/L) | 7.9 | 8.4 | 9.2 | 9.3 | 10.1 |
| Sulfate (mg/L) | 4.6 | 4.7 | 6.2 | 5.0 | 5.0 |
| Cations |  |  |  |  |  |
| Sodium (mg/L) | 135.1 | 140.4 | 147.5 | 150.4 | 157.4 |
| Ammonium (mg/L) | 0.04 | 0.6 | 0.7 | 0.9 | 1.3 |
| Potassium (mg/L) | 19.4 | 20.0 | 21.0 | 21.1 | 21.2 |
| Magnesium (mg/L) | 0.6 | 0.6 | 0.8 | 0.6 | 0.6 |
| Calcium (mg/L) | 2.7 | 3.4 | 2.88 | 2.6 | 2.5 |

TABLE 7

Major ions during leaching test after treatment of diluted supernatant, Phase 2.

|  | Phase 2-1 hr | Phase 2-6 hr | Phase 2-12 hr | Phase 2-24 hr | Phase 2-48 hr |
|---|---|---|---|---|---|
| Anions |  |  |  |  |  |
| Chloride (mg/L) | 10.8 | 10.9 | 11.4 | 11.5 | 11.05 |
| Nitrite (mg/L) | 0.04 | 0.003 | n.a. | 0.01 | 0.015 |
| Nitrate (mg/L) | n.a. | 0.06 | n.a. | 0.007 | 0.0055 |
| Phosphate (mg/L) | 5.9 | 7.9 | 8.8 | 9.1 | 10.35 |
| Sulfate (mg/L) | 10.8 | 11.8 | 12.7 | 11.8 | 11.95 |
| Cations |  |  |  |  |  |
| Sodium (mg/L) | 72.6 | 84.2 | 85.6 | 86.7 | 91.0 |
| Ammonium (mg/L) | 0.4 | 0.5 | 0.9 | 1.1 | 0.6 |
| Potassium (mg/L) | 15.0 | 16.7 | 17.2 | 17.45 | 17.7 |
| Magnesium (mg/L) | 0.4 | 0.6 | 0.6 | 0.5 | 0.5 |
| Calcium (mg/L) | 1.5 | 2.9 | 2.3 | 2.1 | 2.5 |

Some of the general and specific technology described herein may include a method of moderating an environment in an area where animal wastes are collected in a fluid containing compartment. The method may include:

a) collecting animal waste in a fluid containing compartment, the animal waste generating or providing in or above the fluid containing compartment at least one waste selected from the group consisting of carbon dioxide, hydrogen sulfide, ammonia, methane, mercaptans and organic acids;

b) providing in the fluid containing compartment a combination of i) a polymer capable of absorbing at least ten times its weight in water and ii) a combination of salts that react to liberate $I_2$; and c) flocculating an at least one waste with liberated $I_2$ to form a flocculent with the polymer, iodine and waste.

The combination of salts used to provide the iodine may include cupric sulfate and potassium iodide. The polymer in the flocculent may be a hypertonic polymer comprising a superabsorbent polymer with ions from the combination of salts, especially iodine and copper. The polymer may preferably contain acrylic acid, methacrylic acid, acrylic acid salt and/or methacrylic acid salt moieties and may be a superabsorbent polymer.

In the method, the fluid containment compartment may be positioned below ground (it may be above ground, but this might require some pumping action to get the fluid and animal waste to the above ground container) and animal waste from animal housing is fed by gravity from the animal housing into the fluid containment compartment. The compartment may be an open tank, open pool, open storage pond, cement pool or metal pool or tank, or any other closed or open system that stores the animal wastes and liquids and does not allow the material to continually flow out of control. The compartment is positioned below ground and animal waste from animal housing is fed by gravity from the animal housing into the fluid containment compartment to the flocculent and wherein iodine in the fluid containment compartment reduces concentrations of odorous gases evaporating from the fluid in the fluid containing compartment. Usually the method is used where at least one waste is ammonia and the iodine binds ammonia into the polymer and the flocculent is removed from the fluid containment container and spread onto soil to provide agriculturally available nitrogen compounds for plant fertilizer. For example, at least one waste may be ammonia and the iodine binds ammonia into the polymer and the flocculent is removed from the fluid containment container and spread onto soil to provide agriculturally available nitrogen compounds for plant fertilizer, along with available carbon compounds in the waste. The method may also operate where at least one waste is carbon dioxide and the iodine binds carbon dioxide into the polymer and the flocculent is removed from the fluid containment container and spread onto soil to provide agriculturally available carbon compounds for plant fertilizer.

A product of the process is a flocculent that can be used as an anti-leaching fertilizer and soil hydration amendment. The flocculent would contain: i) a superabsorbent polymer, ii) water of hydration and iii) a residue of salts that have previously reacted to liberate $I_2$; and iii) at least some iodide entrapped in the flocculent with the polymer, with at least some iodide in the flocculent sequestering a waste material selected from the group consisting of carbon dioxide, hydrogen sulfide, ammonia, nitrates, nitrites, methane, mercaptans and organic acids. The flocculent would also have some animal waste from urine and feces present in the flocculent. The flocculent would have the residue of salts present as at least 0.001% by weight of the superabsorbent polymer, and up to 50% by weight of the superabsorbent polymer. At least some of the waste material may have been oxidized. The flocculent contains agriculturally available nitrogen fertilizer therein.

What is claimed:

1. A method of moderating an environment in an area where animal wastes are collected in a fluid containing compartment comprising: a) collecting animal waste in a fluid containing compartment, the animal waste generating or providing in or above the fluid containing compartment at least one waste selected from the group consisting of carbon dioxide, hydrogen sulfide, ammonia, methane, mercaptans and organic acids; b) providing in the fluid containing compartment a combination of i) a polymer capable of absorbing at least ten times its weight in water and ii) a combination of salts that react to liberate $I_2$; and c) flocculating an at least one waste collected in a) with liberated $I_2$ to form a flocculent with the polymer, iodine and the at least one waste.

2. The method of claim 1 wherein the combination of salts comprises cupric sulfate and potassium iodide.

3. The method of claim 1 wherein the polymer in the flocculent comprises a hypertonic polymer comprising a superabsorbent polymer with ions from the combination of salts.

4. The method of claim 3 wherein the polymer comprises acrylic acid, methacrylic acid, acrylic acid salt and/or methacrylic acid salt moieties.

5. The method of claim 1 wherein the polymer comprises a superabsorbent polymer.

6. The method of claim 5 wherein the combination of salts comprises cupric sulfate and potassium iodide.

7. The method of claim 1 wherein the fluid containment compartment is positioned below ground and animal waste from animal housing is fed by gravity from the animal housing into the fluid containment compartment.

8. The method of claim 5 wherein the fluid containment compartment is positioned below ground and animal waste from animal housing is fed by gravity from the animal housing into the fluid containment compartment to the flocculent and wherein iodine in the fluid containment compartment reduces concentrations of odorous gases evaporating from the fluid in the fluid containing compartment.

9. The method of claim 1 wherein the at least one waste is ammonia and the iodine binds ammonia into the polymer and the flocculent is removed from the fluid containment container and spread onto soil to provide agriculturally available nitrogen compounds for plant fertilizer.

10. The method of claim 6 wherein the at least one waste is ammonia and the iodine binds ammonia into the polymer and the flocculent is removed from the fluid containment container and spread onto soil to provide agriculturally available nitrogen compounds for plant fertilizer.

11. The method of claim 1 wherein the at least one waste is carbon dioxide and the iodine binds carbon dioxide into the polymer and the flocculent is removed from the fluid containment container and spread onto soil to provide agriculturally available carbon compounds for plant fertilizer.

12. The method of claim 5 wherein the at least one waste is carbon dioxide and the iodine binds carbon dioxide into the polymer and the flocculent is removed from the fluid containment container and spread onto soil to provide agriculturally available carbon compounds for plant fertilizer.

13. A flocculent for use as an anti-leaching fertilizer and soil hydration amendment comprising: i) a superabsorbent polymer, ii) water of hydration and iii) a residue of salts that have previously reacted to liberate $I_2$; and iii) at least some iodide entrapped in the flocculent with the polymer, with at least some iodide in the flocculent sequestering a waste material selected from the group consisting of carbon dioxide, hydrogen sulfide, ammonia, nitrates, nitrites, methane, mercaptans and organic acids.

14. The flocculent of claim 13 wherein animal waste from urine and feces are present in the flocculent.

15. The flocculent of claim 14 wherein the residue of salts is present as at least 0.001% by weight of the superabsorbent polymer.

16. The flocculent of claim 14 wherein at least some of the waste material has been oxidized.

17. The flocculent of claim 15 wherein the flocculent contains agriculturally available nitrogen fertilizer therein.

* * * * *